(12) United States Patent
Wohleb et al.

(10) Patent No.: US 10,941,102 B2
(45) Date of Patent: Mar. 9, 2021

(54) AQUEOUS LEACHING METHOD TO PRODUCE MICROCRYSTALLINE POWDER

(71) Applicants: Robert Henry Wohleb, Bainbridge Island, WA (US); Thomas Jennings Wohleb, Olympia, WA (US); Joseph David Friis, Davis, CA (US)

(72) Inventors: Robert Henry Wohleb, Bainbridge Island, WA (US); Thomas Jennings Wohleb, Olympia, WA (US); Joseph David Friis, Davis, CA (US)

(*) Notice: Subject to any disclaimer, the term of this patent is extended or adjusted under 35 U.S.C. 154(b) by 0 days.

(21) Appl. No.: 16/203,542

(22) Filed: Nov. 28, 2018

(65) Prior Publication Data

US 2019/0359550 A1  Nov. 28, 2019

Related U.S. Application Data

(60) Provisional application No. 62/592,293, filed on Nov. 29, 2017.

(51) Int. Cl.
*C07C 51/42* (2006.01)
*C07D 311/80* (2006.01)
*C07C 51/43* (2006.01)

(52) U.S. Cl.
CPC ............ *C07C 51/42* (2013.01); *C07C 51/43* (2013.01); *C07D 311/80* (2013.01); *C07B 2200/13* (2013.01)

(58) Field of Classification Search
CPC ....... C07C 51/42; C07C 51/43; C07D 311/80; C07B 2200/13
USPC .......................................................... 549/390
See application file for complete search history.

(56) References Cited

U.S. PATENT DOCUMENTS

| | | | |
|---|---|---|---|
| 9,376,367 B2* | 6/2016 | Herkenroth | C07D 311/80 |
| 2002/0086438 A1* | 7/2002 | Elsohly | B01D 15/265 |
| | | | 436/177 |
| 2005/0049298 A1* | 3/2005 | Goodwin | A61K 36/00 |
| | | | 514/453 |
| 2005/0266108 A1* | 12/2005 | Flockhart | C07D 311/80 |
| | | | 424/774 |

(Continued)

FOREIGN PATENT DOCUMENTS

| | | | | |
|---|---|---|---|---|
| WO | WO-2016187679 A1 * | 12/2016 | | A61K 36/185 |
| WO | WO-2019057994 A1 * | 3/2019 | | A61K 2300/00 |

OTHER PUBLICATIONS

Appendino; Current Medicinal Chemistry, 2011, 18, 1085-1099. (Year: 2011).*

(Continued)

*Primary Examiner* — Daniel R Carcanague
(74) *Attorney, Agent, or Firm* — Brubaker Law Group

(57) ABSTRACT

Non-water soluble cannabinoid acids are isolated from trichomes and flower of *Cannabis* genus by leaching with alkaline water. The leaching with alkaline water converts the cannabinoid acids to water soluble salts. The resulting solution of cannabinoid salts may be used as a source of acidic cannabinoids for pharmaceutical applications or the cannabinoid acid salts may be converted back to their acid form and precipitated into a high purity microcrystalline powder by acidification of the aqueous solution. Compounds that are not water soluble and do not form salts in alkaline water such as many pesticides, fungicides and off flavors will not be concentrated.

10 Claims, 6 Drawing Sheets

(56) References Cited

U.S. PATENT DOCUMENTS

| | | | |
|---|---|---|---|
| 2011/0046213 A1* | 2/2011 | Bhatarah | C07D 311/80 514/454 |
| 2015/0038567 A1* | 2/2015 | Herkenroth | C07D 311/80 514/454 |
| 2016/0214920 A1* | 7/2016 | Nadal Roura | B01D 15/26 |
| 2016/0228385 A1* | 8/2016 | Sievers | A61K 33/00 |
| 2016/0326130 A1* | 11/2016 | Changoer | B01D 11/0288 |
| 2017/0008870 A1* | 1/2017 | Dibble | C07D 311/80 |
| 2018/0162828 A1* | 6/2018 | Nadal Roura | B01D 11/0492 |
| 2018/0333446 A1* | 11/2018 | Shan | A61K 36/185 |
| 2019/0010106 A1* | 1/2019 | Oroskar | C07C 37/685 |
| 2019/0160393 A1* | 5/2019 | Marshall | B01D 11/0219 |

OTHER PUBLICATIONS

Mechoulam; Chem. Rev. 1976, 76, 75-112. (Year: 1976).*
Wohlfarth; Journal of Chromatography B, 879 (2011) 3059-3064. (Year: 2011).*
Warner; Forensic Chemistry 2017, 3, 52-57. (Year: 2017).*

* cited by examiner

Compound 101, THCA
(Δ9-tetrahydrocannabinolic acid)

Compound 102, CBDA
(Cannabidiolic acid)

Compound 103, CBGA
(Cannabigerolic acid)

Compound 104, CBCA
(Cannabichromenenic acid)

Figure 6

| Name | pH=13 LogD | pH=13 LogS |
|---|---|---|
| Aflatoxin | 1.37 | -3.98 |
| Azinphos methyl | 2.75 | -3.29 |
| Azoxystrobin | 2.84 | -6.28 |
| Bifenazate | 3.55 | -4.49 |
| Bifenthrin | 6.59 | -7.39 |
| Captan | 2.46 | -3.86 |
| Carbaryl | 2.45 | -3.62 |
| Chlorothalonil | 4.1 | -5.01 |
| Chlorpyrifos | 4.78 | -6.06 |
| DDD | 5.76 | -5.77 |
| DDT | 4.93 | -5.09 |
| Diazinon | 4.19 | -3.89 |
| Dicofol | 3.52 | -4.49 |
| Difenoconazole | 4.3 | -6.00 |
| Endosulfan I | 2.6 | -5.78 |
| Fluvalinate | 6.2 | -5.62 |
| Imazilil | 3.75 | -3.78 |
| Malathion | 1.86 | -2.66 |
| Metalaxyl | 2.12 | -2.83 |
| Parathion | 3.32 | -4.51 |
| pyraclostrobin | 4.08 | -4.44 |
| pyrethrin | 4.06 | -4.49 |
| Tebuthiuron | 1.35 | -2.22 |

AQUEOUS LEACHING METHOD TO PRODUCE MICROCRYSTALLINE POWDER

TECHNICAL FIELD

The present invention relates to plant material extraction processes and products. More specifically, the present invention is directed to extraction methods, and products, and powders of flowers of the *Cannabis* genus.

BACKGROUND

Concentrated or purified cannabinoid acids show great potential as non-psychoactive medicinal materials. Cannabinoid acids are produced and stored in trichomes on surfaces of the *Cannabis* plant. Concentrates or extracts of *Cannabis* have found favor in medicinal research. Extraction of cannabinoids from *Cannabis* to produce these concentrates has historically been accomplished by organic solvent extraction where dehydrated *Cannabis* is washed with an organic solvent. Pre-dehydration of the *Cannabis* prior to extraction is required for efficient organic solvent extraction. Dehydration of the *Cannabis* plant material often causes some conversion of the cannabinoid acids to their decarboxylated form.

Typically the solvents used have been hydrocarbon based solvents or alcohols. Low boiling solvents are normally used to assist in recovery or elimination of the solvent from the extract by heating to vaporize the solvent from the extract or by vacuum distillation. Heating of the concentrate causes at least some additional "activation" or decarboxylation of the acids. For example the naturally occurring non-psychoactive delta 9-THC-acid can be converted to the psychoactive delta 9-THC by heating. All of these solvents are flammable which may cause safety issues. None of these solvent systems produce a high purity product as the extraction lacks specificity. Hydrocarbons will extract most hydrophobic compounds including high molecular weight lignin, lignans, gums, lignocellulosic material, and the like along with the cannabinoids. Ethanol is more polar than hydrocarbons and therefore also extracts some of the water soluble materials. Concentrates from the organic solvent systems require extensive cleanup in order to produce high purity cannabinoid acids.

One such hydrocarbon extraction device utilizes butane as a solvent where the pressurized liquid butane is passed through the plant material in order to effect extraction of the cannabinoids. Residual solvent evaporated from the concentrate under heat/vacuum and is typically released into the atmosphere. Attempts are often made to recycle butane but this is not 100% efficient and hydrocarbons are released to the atmosphere. The concentrate is known as BHO for butane hash oil. U.S. Pat. No. 9,327,210 discloses butane extraction devices and methods of butane extraction.

U.S. Pat. No. 9,044,390 discloses a method for forming *Cannabis* concentrates utilizing supercritical fluids with solvent pressure between 750 psi and 25,000 psi and at temperatures between −15° C. and 200° C. The equipment used for supercritical fluid extraction is expensive and must be operated by highly trained technicians. Plant material dehydration is required as with hydrocarbon extraction.

Concentrates from the foregoing extraction technologies as well as others have strong taste and odor which they impart to edibles. Further these concentrates are in a solid or viscous form and are difficult to mix with food products. Additionally it is difficult to accurately dose edibles or drinks using these concentrates.

Additionally, the solvents and techniques used tend to not discriminate against most pesticides, fungicides or herbicides and instead tend to concentrate these compounds in the final extract or concentrate. It is often found that concentrates will not pass threshold levels when made from plant material that previously passed threshold levels.

The use of these concentrates to infuse into other products such as smoking materials to increase cannabinoid content is also difficult due to the oily nature and high viscosity.

It would be desirable to have a process for extracting acidic cannabinoids directly from green plant surfaces of *Cannabis* genus without having to first dehydrate the plant material. Furthermore, it would be desirable to be able to use water as the leaching agent for cannabinoids eliminating the use of expensive organic solvents which are potentially polluting. Additionally it would advantageous to have a process that rejects pesticides, fungicides and herbicides. Still further, it would be desirable to have a process for extracting cannabinoids that did not require equipment that is typically expensive and uses high temperature and/or pressure to accomplish the extraction of cannabinoids. It would further be desirable to be able to produce a high purity microcrystalline cannabinoid powder from this aqueous leachate. Still further, it would be desirable to be able to leach acidic cannabinoids from existing solvent extracts. It would further be desirable to have a microcrystalline cannabinoid powder that is easy to disperse into edible products. It would additionally be desirable to have a cannabinoid powder that is essentially odorless and tasteless. Therefore, there currently exists a need in the industry for a simple and inexpensive process that produces a tasteless and odorless cannabinoid powder using an aqueous extraction solvent that can be applied directly to plant surfaces or extracts.

SUMMARY OF THE INVENTION

The present invention discloses methods to extract cannabinoids from flower of the *Cannabis* genus using alkaline water to produce a microcrystalline cannabinoid powder. Alternatively, the invention may use trimmings from freshly harvested flower of *Cannabis* genus or previously dehydrated *Cannabis* plant material.

BRIEF DESCRIPTION OF DRAWINGS

The present invention will become more fully understood from the detailed description and accompanying drawings, which are not to scale.

FIG. 6 list of discriminated pesticides etc.

DETAILED DESCRIPTION

Figure 1:
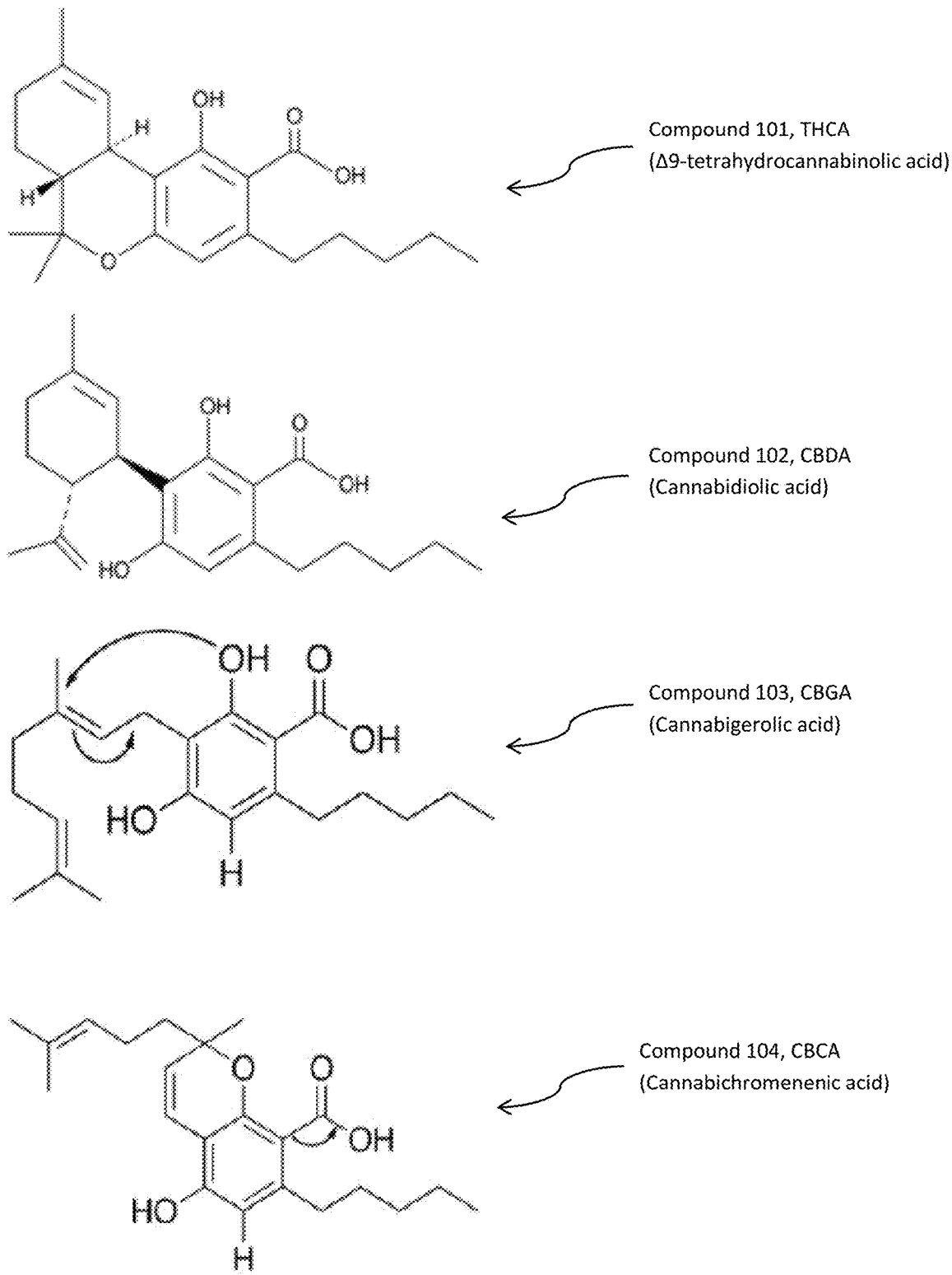
FIG. 1 Typical Cannabinoid acids found in *Cannabis*.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

For the purpose of these disclosures the term leaching is used where soluble substances are removed from a surface by percolation of an aqueous solution as opposed to solvent extraction. The term leachate refers to the aqueous solution after it has removed substances from a surface. The term countercurrent leaching is used to describe leaching where the leaching solution flows in an opposite direction to that of the material being leached. The term microcrystalline powder is used to describe a crystallized substance or powder that contains small crystals visible only through microscopic examination. Log P is used here to describe the partition coefficient of a molecule between an aqueous and lipophilic phases when in an uncharged state. Log D is similar to log P but is pH dependent, hence one must specify the pH at which the log D was measured. In these disclosures both log P and log D refer to the hydrophobic or lipophilic character of a molecule.

Disclosed herein are methods for leaching non-water soluble cannabinoid acids directly from plant surfaces and trichomes utilizing water with pH control as a leaching agent, in a batch or continuous countercurrent manner. Other insoluble organic acids could be leached from other vegetation surfaces and trichomes however this method may be ideally suited to cannabinoid acids. Further disclosed are methods for utilizing water with pH control to extract acidic cannabinoids from other materials including concentrates from existing extraction technologies.

Still further disclosed is a method for forming a cannabinoid microcrystalline powder from the alkaline aqueous leachate again utilizing pH control, the microcrystalline powder being essentially odorless and tasteless.

Additionally disclosed is a method for excluding off flavors, pesticides, fungicides, herbicides and the like from the final product or microcrystalline cannabinoid powder.

Figure 2:
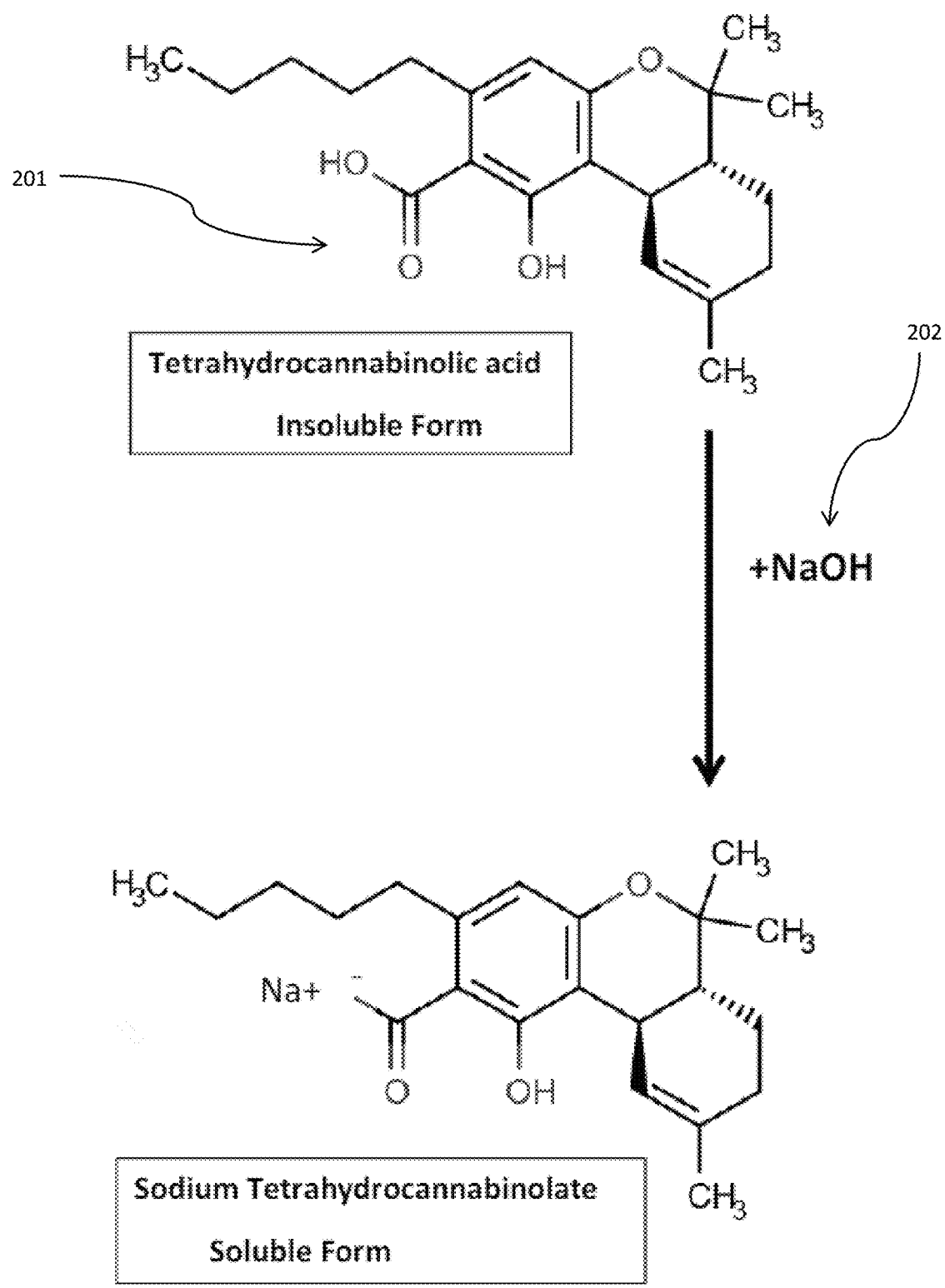
FIG. 2 Forming soluble salts of cannabinoid acids.

Non water soluble acidic cannabinoids may be synthesized primarily within glandular trichomes on the surface of the *Cannabis* plant. The typical cannabinoid acids may be considered to be non-psychotropic to have potential pharmaceutical properties. FIG. 1 is a list with chemical structures of common cannabinoid acids found on the plant surface. Compound 101 THCA ($\Delta^9$-tetrahydrocannabinolic acid) and Compound 102 CBDA (Cannabidiolic acid) are common acids found on the surface of the *Cannabis* plant. FIG. 1 also shows two other cannabinoid acids commonly found on the surface of the *Cannabis* plant. Compound 103 is CBGA (Cannabigerolic acid) the precursor for THCA and Compound 104, CBCA (Cannabichromenenic acid). Cannabinoid acids may be classified as weak organic acids. Weak organic acids may react with strong inorganic bases to form salts with increased water solubility. FIG. 2 shows Compound 101 THCA forming the sodium salt sodium tetrahydrocannabinolate (item 201) when sodium hydroxide (item 202) is used to raise the pH of water. The higher the pH the more salt is formed and the greater the solubility.

Figure 3:
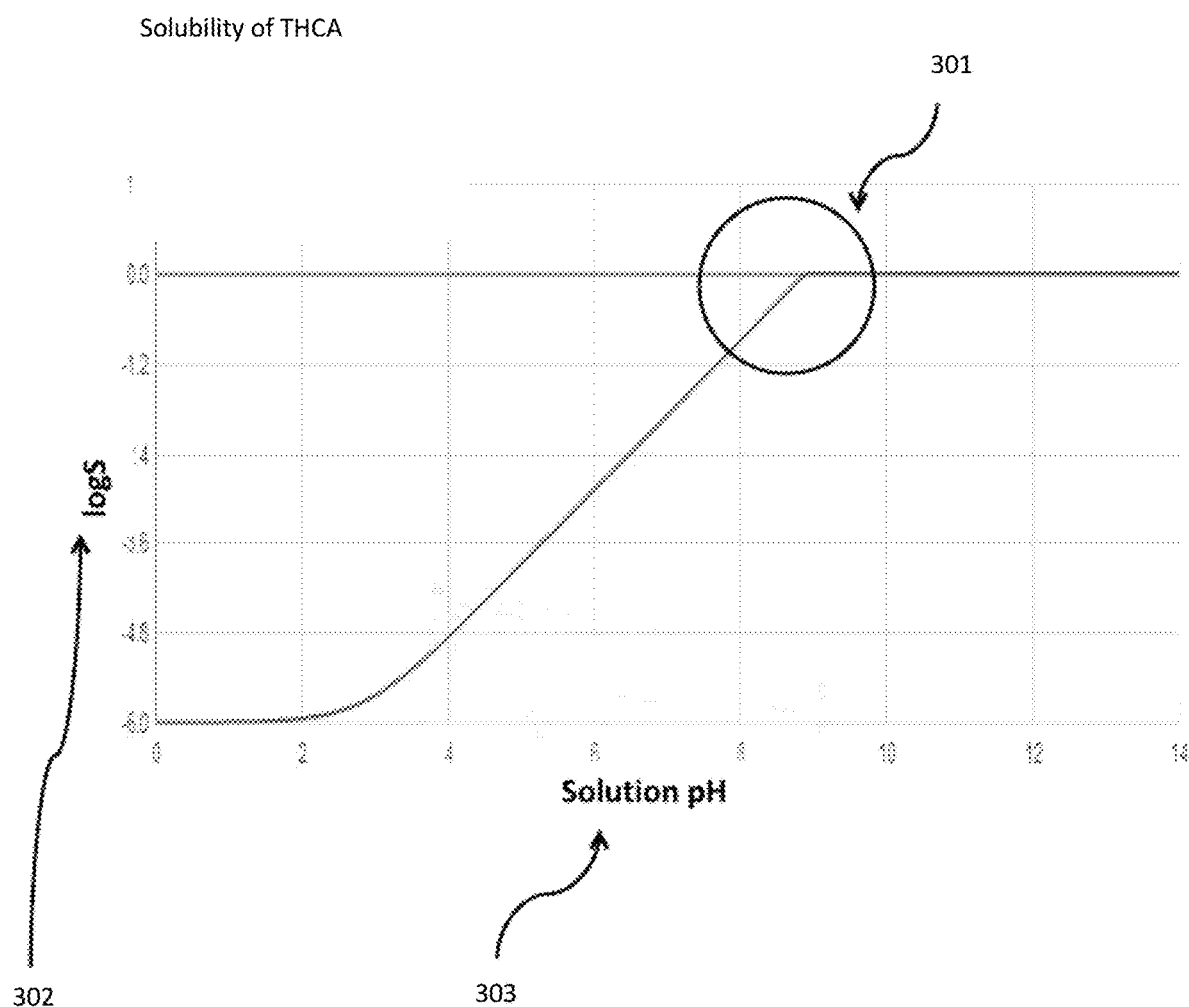
FIG. 3 Typical Log S vs pH curve for cannabinoid acids.

For the case of cannabinoid acids, intrinsic solubility may be defined as the equilibrium solubility of the free acid at a pH where it is fully un-ionized. Where intrinsic solubility is very low it may be convenient to use log S as a measure of solubility where S is the solubility at a temperature of 20-25° C. in mol/L. Calculated intrinsic solubility for THCA may be −5.99 at a pH of 1.5. FIG. 3 is a plot of calculated solubility for Compound 101, THCA, as log S, 302, plotted against solution pH, 303. It can be seen that item 301 at a pH=8.8 that log S is equal to 0 or equal to 1 mol/L. Increasing pH above 8.8 causes additional increases in log S and solubility. Each change in pH ±0.1 may change the solubility of the cannabinoid acid 10 fold. THCA is used here as an example. There may be slight differences in log S plots for the other cannabinoid acids.

In theory any pH greater than approximately 8.8 may provide adequate solubility of the cannabinoid acids in water for an efficient leaching. Each embodiment may have different extraction requirements so that in practice each embodiment of this invention has an optimal range of pH. For example, freshly harvested plant material may still have intact cuticle which protects the plant interior from leaching of non-cannabinoid acids that would potentially reduce the purity of the final product. This allows for more aggressive leaching of intact plant surfaces.

Figure 4:
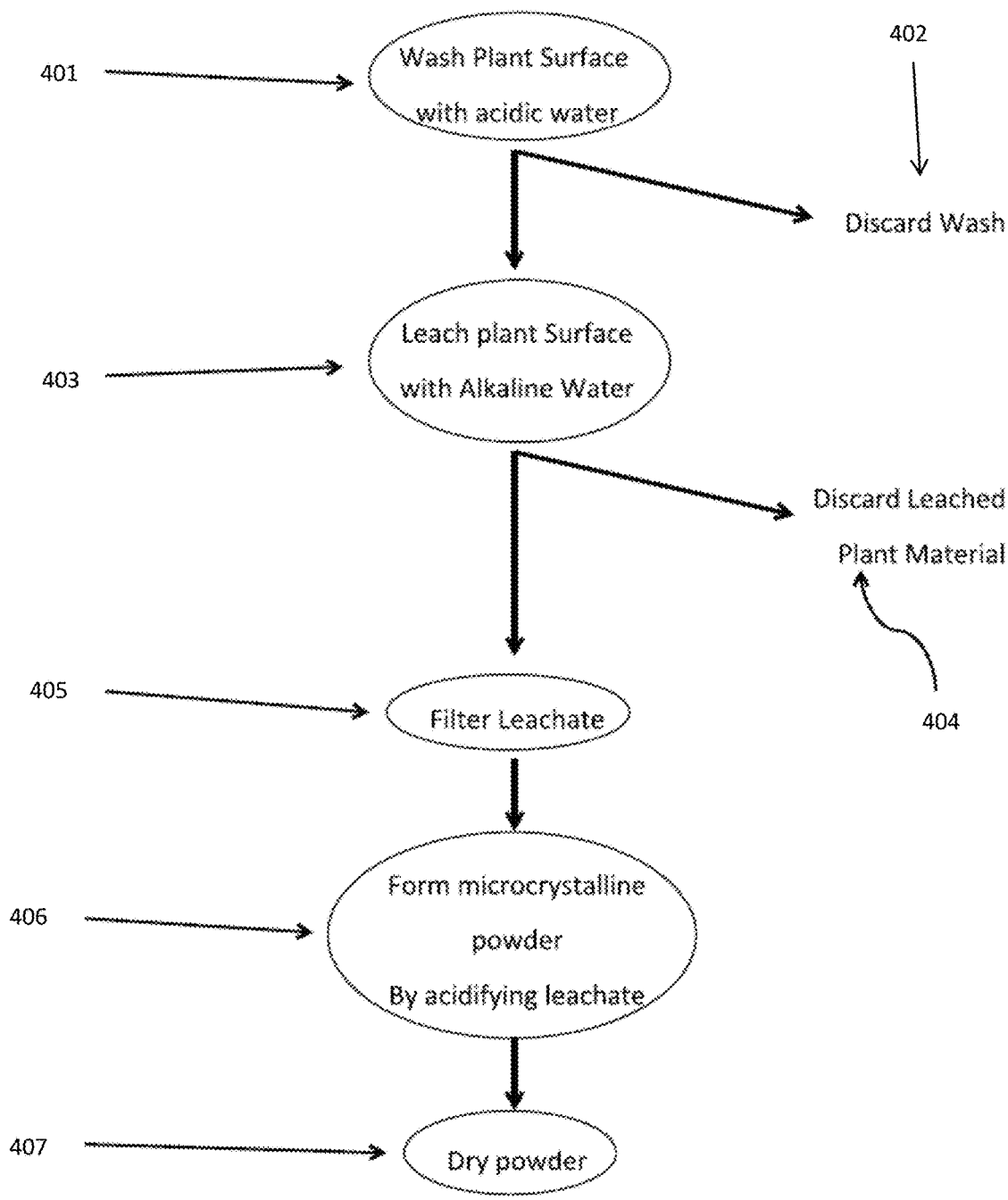
FIG. 4 is a process chart for leaching plant material.

In a preferred embodiment, the surface of freshly harvested *Cannabis* flower is the primary source of cannabinoid acids. FIG. 4 is a flowchart depicting the essential elements of the process. In an optional step 401, the freshly harvested plant material is first washed with water at a pH≤7 in order to remove water soluble plant materials. The wash water containing the water soluble materials from the plant surface is discarded in step 402. These water soluble materials are waste that could potentially interfere with product purity. In step 403, the plant material is leached with alkaline water having a pH range of 11.0 to 12.3 depending on whether the extraction is done in a batch or more efficient countercurrent fashion. When possible a lower pH is preferred as higher pH may solubilize unwanted compounds such as lignins. Sodium hydroxide is typically used for the pH adjustment as it is a strong base and easily forms salts of cannabinoid acids. It is important at step 403 that all of the surface containing trichomes come in contact with the leaching solution. This typically requires agitation. The amount of agitation required is dependent upon the plant maturity and type. Immature flower of *Cannabis* has fairly closed bud requiring more agitation while more mature flower is more open and requires less. The actual required contact time of the alkaline water with the plant surface may be relatively short, typically 20 to 30 seconds. In step 404, the leached plant material, is now largely depleted of cannabinoid acids, and is discarded. The leachate from step 403 now contains the soluble salts of the cannabinoid acids. The leachate is then filtered to remove extraneous non soluble plant material in step 405. Filtration down to at least 1 micron insures adequate leachate clarity. At this point in the process, the clarified leachate from step 405 may be used as a source for further separation into its individual components by chromatography and the like.

Alternatively, as indicated in step 406, the leached cannabinoids may be precipitated by acidifying (FIG. 2, item 202) the leachate converting the cannabinoid salts back to their non- or low solubility form as cannabinoid acids. Referring again to rapid precipitation in this manner causes the formation of microcrystals of the collected cannabinoids. The precipitate is collected by filtration, for example with a Buchner funnel, in step 407 and air dried with low humidity into a white or off-white microcrystalline powder. The color of the powder can be affected by the ratio of cannabinoid acids leached from the plant surface.

The preferred embodiment may be done batch-wise with aqueous solutions held in vessels such as buckets or barrels. Leaching solution may be placed in multiple barrels so that the *Cannabis* flower may be leached multiple times by going from bucket to bucket or processed in a countercurrent fashion with a screw type conveyor.

In an additional embodiment the starting material may be frozen or previously frozen but not dehydrated plant material. Processing also follows the general guidelines and flow as depicted above in FIG. 4.

In an alternate embodiment the starting material may be previously dehydrated *Cannabis* flower or trim. The process follows the same flow chart as in FIG. 4 except that step 401 is preferred rather than optional. With dry material, step 401 may serve an additional function by rehydrating the dry material. Rehydrated plant material may function in a similar manner to fresh plant material. Non-rehydrated plant material may present more than the cuticle protected surface of the plant material to the leaching solution allowing solubilizing of non-cannabinoid acids and requires further purification steps.

Figure 5:
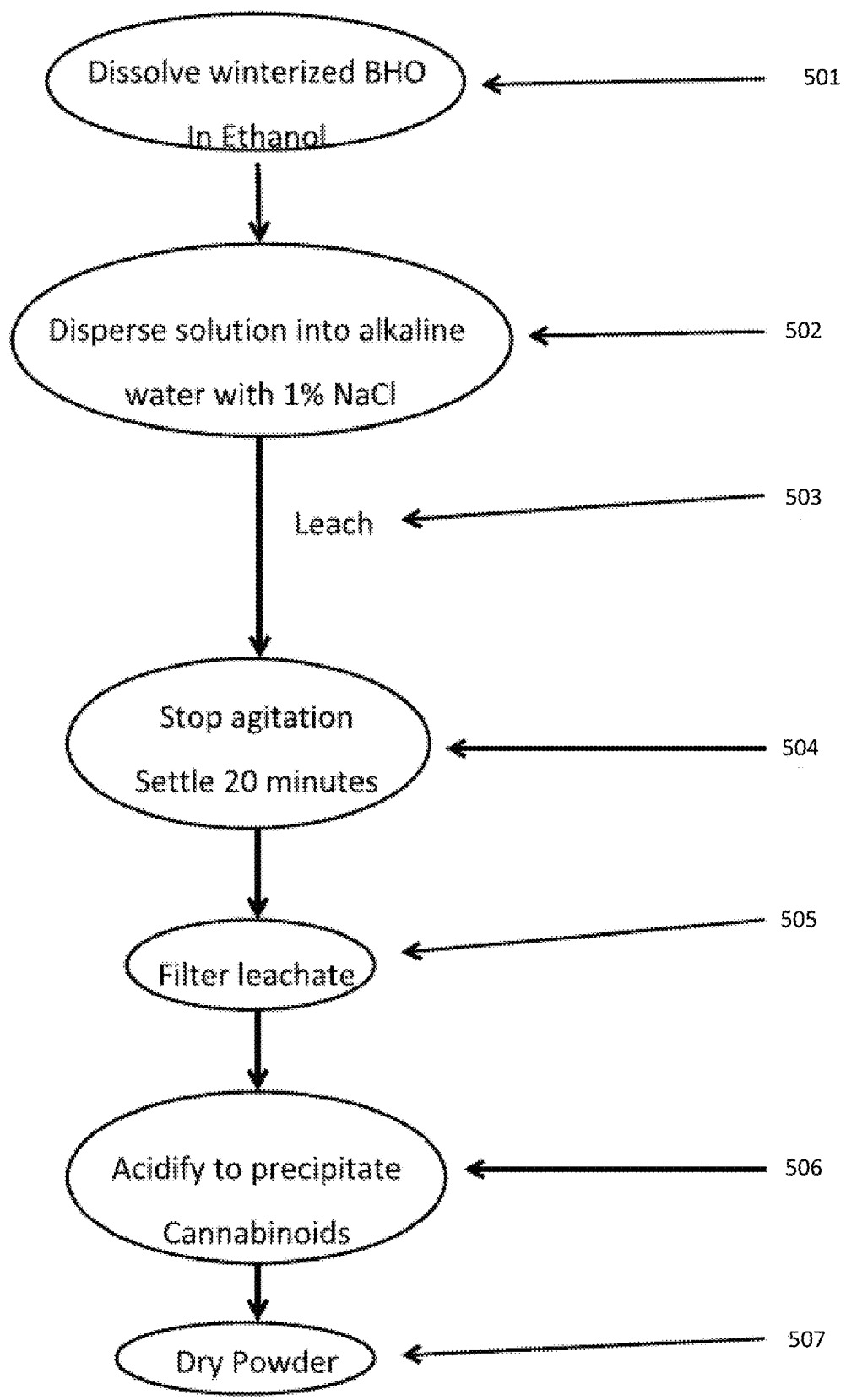
FIG. 5 is a process chart for leaching winterized BHO.

In still another embodiment, the starting material is a *Cannabis* extract or concentrate such as BHO (butane hash oil), CO2 oil or "distillates", which is leached with alkaline water from which microcrystalline cannabinoid powder is produced. In this method, the process of solubilizing cannabinoid acids by alkaline leaching may be applied in a similar fashion to purify hydrophobic mixtures or oils previously extracted from the *Cannabis* genus. The solubilized salts may then be used for downstream operations or precipitated into a microcrystalline powder. FIG. 5 depicts the elements of this process in a flow chart. As it applies to BHO (Butane Hash Oil) the BHO must first be winterized by any procedure known in the art. The winterized BHO is first dissolved, 501, in 190-proof ethanol at a rate of approximately 1,000 grams of BHO to each gallon of ethanol. The alcohol/BHO solution is rapidly dispersed, 502, into an alkaline solution containing 1% sodium chloride forming an emulsion. We typically use a pH of 11.5 to 11.6 and a ratio of alcohol/BHO solution to alkaline aqueous solution of 1:80. These conditions are not limited in scope but solely example of suitable conditions. The emulsion formed is agitated for about 20 minutes, 503, during which time the cannabinoid acids are solubilized by leaching from the lipophilic emulsified droplets. In step 504, the agitation is turned off and the leached particles are allowed to settle. In step 505, the leachate is clarified by filtration, centrifugation or other methods known in the art. We typically filter down to 0.5μ. In step 506, the leachate is rapidly acidified to a pH of usually less than 3 causing conversion of the cannabinoid salts back to the insoluble acid state causing precipitation in a microcrystalline form. The precipitate is collected by usual ways known in the art including filtration or centrifugation then dried, step 507, to form powder.

In an additional embodiment, the characteristics of the leaching process may be used to discriminate against concentrating most pesticides, fungicides, herbicides, off flavors and the like. Compounds that have a high log D and a negative log S will not be appreciably leached by the alkaline leaching solution and will therefore not contaminate the final microcrystalline powdered cannabinoids. FIG. 6 is a list of commonly tested for mycotoxins, pesticides and fungicides which will not be leached by the alkaline solution. Column 601 gives the names in the list. Column 602 gives the log D at pH 13 and Column 603 gives the log S of each compound. As can be seen in FIG. 6 these compounds all have a positive log D and negative log S.

In an alternative embodiment leaching of cannabinoid acids from plant surfaces may be done in a countercurrent fashion either as batches or continuous flow.

In still another embodiment, the starting material is a *Cannabis* extract or concentrate such as BHO (butane hash oil), CO2 oil or "distillates", which is leached with alkaline water from which microcrystalline cannabinoid powder is produced.

Additionally, in another embodiment the starting material is any material that contains contaminants such as pesticides or off flavors which is leached with alkaline water such that the microcrystalline cannabinoid powder produced is free of off flavors or pesticides.

In an additional embodiment an alkaline extract containing salts of cannabinoid acids is used as starting material for purification of individual cannabinoids.

Certain embodiments of the present invention include the foregoing presented embodiments, but are not limited to them.

The following examples utilize a batch process, are purely illustrative and are not meant to be limiting in application or scope of process.

Examples

Leaching of Cannabinoid Acids from Fresh Plant

| | |
|---|---:|
| Total mass of freshly harvested cannabis plant material = | 991 Kg |
| Volume of aqueous leaching solution containing 0.5% = | 7,570 L |
| NaCl and adjusted to a pH of 12.3 with NaOH | 14.3 Kg |
| Mass of microcrystalline powder obtained = | |
| Percent THCA by HPLC analysis = | 91.93% |
| Percent CBDA by HPLC analysis = | 6.94% |
| Total acidic cannabinoids = | 98.87% |

Leaching of Cannabinoid Acids from Dehydrated Bud Material

| | |
|---|---|
| Total mass of cured (dehydrated) bud designated for oil production. = | 30.4 Kg |
| Volume of water rinse at a pH of 6.5 adjusted by the addition of HCl = | 625 L |
| Volume of alkaline leaching solution with 0.5% NaCl adjusted to a pH of 11.5 with NaOH = | 1,150 L |
| Mass of microcrystalline powder obtained = | 3,040.8 gr |
| Percent THCA by HPLC analysis = | 89.23% |
| Percent CBDA by HPLC analysis = | 6.75% |
| Total acidic cannabinoids = | 95.98% |

Leaching of Cannabinoid Acids from BHO

A combination of BHO samples containing off flavors etc. were combined into one lot for leaching.

| | |
|---|---|
| Total Mass of BHO to be processed prior to winterization = | 1.26 Kg |
| Volume of alkaline leaching solution with 1.0% NaCl adjusted to pH 11.8 with NaOH = | 475 L |
| Mass of microcrystalline powder obtained = | 0.95 Kg |
| Percent THCA by HPLC = | 86.87% |
| Percent CBDA by HPLC = | 3.44% |
| Percent CBCA by HPLC = | 4.49% |
| Percent THCVA by HPLC = | 1.22% |
| Total acidic cannabinoids = | 96.02% |

We claim:

1. A method of obtaining acidic cannabinoids from plant material comprising: adding a hydroxide base to water to produce an alkaline solution; exposing plant material to the alkaline solution; removing non-soluble plant material; and acidifying to precipitate cannabinoid acids; wherein the alkaline solution does not comprise an organic solvent.

2. The method in claim 1 wherein the base used is Sodium Hydroxide.

3. The method of claim 1 wherein the cannabinoid acid is THCA.

4. The method of claim 1 wherein the cannabinoid acid is CBDA.

5. The method of claim 1 wherein the plant material is the exposed surface of the exterior of *Cannabis* plant.

6. The method of claim 5 wherein the plant material has a moisture content greater than 50% by weight.

7. The method of claim 5 wherein the plant material is dehydrated.

8. The method of claim 1 wherein plant material is exposed in a countercurrent fashion.

9. The method of claim 8 wherein the countercurrent fashion is accomplished by using a series of containers.

10. The method of claim 8 wherein the counter current fashion is accomplished by using a screw conveyor.

* * * * *